United States Patent [19]

Schmidt et al.

[11] Patent Number: 4,698,387

[45] Date of Patent: Oct. 6, 1987

[54] ALLOSTERIC CONJUGATES OF HEMOGLOBIN AND USE AS BLOOD SUBSTITUTES

[75] Inventors: Karl-Heinz Schmidt, Wankheim; Wolfgang Feller, Melsungen, both of Fed. Rep. of Germany

[73] Assignee: Intermedicat GmbH, Emmenbrucke, Switzerland

[21] Appl. No.: 665,354

[22] Filed: Oct. 26, 1984

[30] Foreign Application Priority Data

Nov. 10, 1983 [DE] Fed. Rep. of Germany ....... 3340592

[51] Int. Cl.$^4$ ...................... C07G 7/00; C07C 103/52; A61K 37/00; A61K 31/71
[52] U.S. Cl. ................................. 525/54.1; 530/350; 530/402; 530/813; 530/816; 514/2; 514/6; 514/7; 514/8; 514/54; 514/59; 514/60
[58] Field of Search .................... 514/2, 6, 7, 8, 54, 514/59, 60; 530/350, 402, 813, 816; 525/54.1

[56] References Cited

U.S. PATENT DOCUMENTS

| | | | |
|---|---|---|---|
| 3,925,344 | 12/1975 | Mazur | 530/385 |
| 4,301,144 | 11/1981 | Iwashita et al. | 514/6 |
| 4,377,512 | 3/1983 | Ajisaka et al. | 424/101 |
| 4,421,896 | 12/1983 | Dorman | 525/54.1 |
| 4,425,334 | 1/1984 | Hunt | 424/101 |

FOREIGN PATENT DOCUMENTS 2616086  4/1976  Fed. Rep. of Germany .
3029307  3/1982  Fed. Rep. of Germany .

OTHER PUBLICATIONS

Tam et al, "Soluble Dextran-Hemoglobin Complex as a Potential Blood Substitute", *Proc. Natl. Acad. Sci.*, vol. 73, No. 6, pp. 2128-2131, Jun. 1976.

Ajisaka et al, "Modification of Human Hemoglobin with Polyethylene Glycol: A New Candidate for Blood Substitute", *Biochem. Biophys. Res. Comm.*, vol. 97, No. 3, pp. 1076-1081, Dec. 1980.

*Primary Examiner*—John Kight
*Assistant Examiner*—Nathan M. Nutter
*Attorney, Agent, or Firm*—Kenyon & Kenyon

[57] ABSTRACT

The invention relates to an allosterically active conjugate composition comprising one or more hemoglobin tetramers and one or more adducts of a physiologically safe macromolecular agent covalently linked to one or more ligands, such that the adduct is bound to the allosteric binding site of the hemoglobin in a reversible, non-covalent manner; the invention also relates to methods for producing such conjugate compositions; and to blood substitutes or plasma extenders containing such conjugates.

26 Claims, 5 Drawing Figures

O₂-binding curve of (a) natural hemoglobin; (b) crosslinked hemoglobin (prior art); (c) myoglobin.

$O_2$-binding curve of a BHP dextran-ATP-HbA conjugate (1 mM);
$P_{50}$=55.00 mbar

Fig. 3.

$O_2$-binding curve of a BHP dextran IHP-HbA conjugate (10 mM);
$P_{50}$=68.62 mbar

Fig. 4.

O₂-binding curve of a BHP dextran-ATB=HbA conjugate (0.2 mM);
$P_{50}$ = 21.01 mbar

Fig. 5.

O₂-binding curve of a BHP dextran-IHP-HbA conjugate (1.0 mM);
$P_{50}$ = 30.15 mbar

ALLOSTERIC CONJUGATES OF HEMOGLOBIN AND USE AS BLOOD SUBSTITUTES

BACKGROUND OF THE INVENTION

The loss of blood or plasma caused by surgery or injuries can be compensated by infusions of whole blood, or by the infusion of blood substitutes or plasma extenders which are capable of oxygen transfer.

Due to the well known problems related to the cost, availability and safety of whole blood, attempts have been made to provide blood substitutes capable of transferring oxygen. There are currently two basic approaches towards achieving this end.

First, fluorocarbons may be used as gas transporting substitutes for blood (*Med. Welt* 32:1338 (1981) and *Med. Lab. Sci.* 39:45 (1982)). A disadvantage of the fluorocarbon emulsions is that they are not completely eliminated from the body, nor are they degraded. Instead they accumulate in organs such as the liver or spleen and remain for at least several years. Widespread use of fluorocarbons is further hindered by the fact that an oxygen-rich atmosphere is required for respiration. Fluorocarbons are also unstable in storage.

The second approach is to use hemoglobin-containing solutions with an oxygen-transferring function as blood substitutes or plasma extenders. Ordinary solutions of stroma-free hemoglobin are not suitable as blood substitutes because of their rapid physiological turnover. Hemoglobin which is not bound by erythrocytes decomposes relatively quickly into its sub-units; these sub-units have a molecular weight of less than 64,500 daltons, and are promptly eliminated by the kidneys.

There have been attempts at improving the efficacy of this second approach by preventing the dissociation of hemoglobin into its sub-units, thereby increasing the intravasal half life. For instance, hemoglobin has been cross-linked intramolecularly or intermolecularly with suitable bifunctional cross-linking agents so as to obtain a molecule size which will ensure a longer residence in the circulation. In this regard, German Offenlegenschrift DE-OS No. 24 17 619 describes plasma protein substitutes which contain hemoglobin where the sub-units are cross-linked to polymers of mean molecular weights between 68,000 and 600,000 with the aid of dialkyl dicarboxylic acid imidates. Alternatively cross-linkage may occur intermolecularly between different hemoglobin tetramers or simultaneously intra- and/or intermolecularly.

German Offenlegenschrift DE-OS No. 26 07 706 also discloses water-soluble hemoglobins, the sub-units of which are cross-linked to polymers with molecular weights of 64,000 to 1,000,000 by means of suitable cross-linking agents, including triazines, multi-substituted polyfunctional benzene derivatives, linear or cyclic polyfunctional poly-alkylene derivatives, dicarboxylic acid derivatives, or dialdehydes. Intermolecular cross-linking of hemoglobin tetramers is also described. The subject of Published European Patent Application EP-A No. 81 301 535.1 is a method for producing artificial red blood cells which contain aqueous, stroma-free hemoglobin solutions in membranes of polymerized hemoglobin. The crosslinking agents of German Offenleigen-schrift DE-OS No. 26 07 706 are used to polymerize hemoglobin and thus to prevent its rapid degradation in the body.

Another way to increase the intravasal half life of stroma-free hemoglobin in the body is to bind hemoglobin covalently to physiologically safe high-polymer materials. Physiologically compatible polymers include hydroxy-ethyl starch (German Offenlegenschrift DE-OS No. 26 16 086) and other polysaccharides which are covalently bound by way of bridges (German Offenlegenschrift DE-OS No. 30 29 307); insulin (published European patent application EP-A No. 81 302 858.6), dextran (Thamm, et al., *Proc. Nat. Acad. Sci. USA*, 73:2128 (1976); Humphries et al., *Proc. B.P.S.*, 191 (1981); Baldwin et al., *Tetrahedron* 37:1723 (1981); and polyethylene glycols of different molecular weights (Ajisaka et al., *Bioch. Biophys. Res. Comm.* 97:1076 (1980); U.S. Pat. No. 4,301,144).

All of the known hemoglobin-containing molecules with high molecular weight share the problem that the covalent bond between the hemoglobin and the cross-linking agent or polymer changes the quaternary structure of that protein component of the hemoglobin which is responsible for oxygen transport, and thus adversely affects the natural properties of the hemoglobin. Although such deoxygenated hemoglobin can bind oxygen, the oxygenated hemoglobin can no longer adequately release the bound oxygen in the peripheral tissue. This increase in oxygen affinity is demonstrated by a shift of the central portion of the oxygen dissociation curve to the left, so that the oxygen dissociation curve for natural hemoglobin represents a lower percentage of oxygen saturation at a given oxygen partial pressure than the corresponding curves for covalently bound hemoglobin compounds as described in the art, which more nearly resemble the hyperbolic curve for myoglobin than the curve for natural hemoglobin.

As the quaternary structure of natural hemoglobin is disturbed by covalent bonds between the protein component and the crosslinking agents or polymer molecules, these cross-linked or polymer-bound hemoglobins show a reduced subunit cooperativity with respect to the binding ability for oxygen. The effect can be measured quantitatively in terms of the reduction in the Hill coefficient, which decreases from 2.8 to lower values. Thus, the curve for cross-linked or polymer-bound hemoglobin derivatives bears greater resemblance to the hyperbolic form of the curve for myoglobin than to the sigmoidal curve form typical of functionally intact hemoglobin.

The relationship between an increase in molecular size brought about by cross-linkage or attachment of the hemoglobin to polymers and an undesired increase in oxygen affinity makes this approach disadvantageous for use as a blood substitute. This disadvantage cannot be eliminated by attaching allosteric effectors to the phosphate bond site of cross-linked hemoglobin in an effort thus to improve the oxygen-yielding ability of the cross-linked or polymer-bound hemoglobins. German Offenlegenschrift DE-OS No. 27 14 252 describes methods for cross-linking hemoglobin with dialdehydes where the hemoglobin contains pyridoxal-5-phosphate instead of the allosteric modulator 2,3 - diphospeoglyceate naturally bound to the phosphate bond site.

The method of German Offenlegenschrift DE-OS No. 31 44 705 follows the same approach, using inositol hexaphosphate as allosteric modulator. While the introduction of the modulator improves the oxygen-yielding ability, the allosterically modified hemoglobin preparations suffer from the disadvantages that result from intramolecular cross-linkage of the hemoglobin subunits, or intermolecular cross-linkage of hemoglobin tetramers. None of the preparations known in the art are suitable for broad therapeutic use.

Thus, there remains a need for a hemoglobin-containing blood substitute which is suitable as an oxygen and carbon dioxide carrier, is capable of oxygen uptake and release under natural conditions, and does not have the foregoing disadvantages.

SUMMARY OF THE INVENTION

It is an object of this invention to provide compositions, and methods for the use thereof, which act as effective blood substitutes and which avoid the disadvantages inherent in previously disclosed compositions and methods.

It is another object of this invention to provide compositions, and methods for the production thereof, which act as blood substitutes which are suitable as oxygen and carbon dioxide carriers and are capable of oxygen uptake and release under natural conditions and which are suitable for broad therapeutic use.

It is a further object of this invention to provide effective blood compositions, and methods for the production thereof, wherein the binding interactions of the hemoglobin molecules with one another are not disturbed by cross-linkage or covalent attachment to polymers, which alters the cooperative behavior of the hemoglobin monomers with respect to their bonding to molecular oxygen, and wherein the composition allows for a long intravasal hemoglobin half-life without rapid elimination through the kidneys.

These and other objects of the invention are achieved by compositions, and methods for the production thereof, which act as blood substitutes and which comprise a conjugate of one or more hemoglobin tetramers and one or more adducts which are made up of one or more ligands and a physiologically acceptable macromolecular agent. The adduct is bound to the allosteric binding center of the hemoglobin by means of its ligand portion. Suitable ligands include sugar phosphates, nucleotides phosphates, pryridoxal phosphate and inositol phosphates. Suitable macromolecular agents include polymers, and liposomes. A preferred embodiment of the macromolecular agent has a molecular weight of about 400 D to about 500,000 D.

The invention further comprises a method for producing such compositions as well as the conjugate compositions together with a physiologically acceptable carrier.

DETAILED DESCRIPTION

The composition of the invention comprises a conjugate between an adduct and hemoglobin, wherein the adduct is made up of an anionic ligand and macromolecular agent.

The macromolecular agent of the adduct includes polymers such as polyvinylprolidone polyvinyl alcohols, polysaccharides, soluble starches, hydroxyalkyl starches of different degrees of substitution, mucopolysaccharides, polyethylene glycols and polypropylene glycols and copolymers thereof and water-soluble, physiologically acceptable derivatives of said polymers, proteins, surfactants, polyols, and polymethylacrylates and derivatives of said compounds. Other suitable macromolecular agents include liposomes, and emulsions of oil in water.

The polymeric, water-soluble, physiologically acceptable compounds which may act as the macromolecular agent contain per monomer unit one or more polar groups, preferably hydroxy, amino, and/or carboxyl groups. Naturally occuring polymers are preferred for the conjugates of the invention, but synthetic polymers and their derivatives may be employed as well.

Preferred polymers are dextran and its derivatives, polyethylene glycols and derivatives thereof; especially preferred are 3-bromo-2-hydroxypropyl dextran, alpha, omega-disubstituted derivatives of polyethylene glycol, and diglycidyl ether of polyethylene glycol.

The preferred molecular weight of the macromolecular agent of the invention is from about 400 D to about 500,000 D; macromolecular agents with molecular weights of from about 400 to about 50,000 D are most preferred.

The macromolecular agents of the adduct are further characterized in that they are chemically linked with ligands, which are low molecular weight substances that can attach themselves to the phosphate binding site of the hemoglobin by way of non-covalent bonds. These ligands permit control of the oxygen affinity of the hemoglobin.

The ligand molecules are usually present in anionic form, and include the ligands naturally bound to hemoglobin, sugar phosphates, inositol phosphates, inositol sulfates, nucleotide phosphates, pyridoxal phosphate and sulfate, sulfated mucopolysaccharides, beta-naphtolphosphates, salicylic acid, p-hydroxygenzoic acid, aromatic aldehydes, and benzenesulfonic acids as well as the derivatives of all the foregoing ligand molecules. Preferred ligand molecules are sugar phosphates, nucleotide phosphates, pyridoxal phosphates, and inositol phosphates, and their derivatives.

Inositol hexaphosphahte is regarded as an especially preferred ligand, as it forms a bond with hemoglobin which is more than ten times stronger than that formed by the modulator 2,3-diphosphoglycerate, which is contained in intact erythrocytes.

Where necessary, the macromolecular agent and the ligand may be connected by a spacer. Spacers include those molecules which carry at each of two ends a functional group capable of binding and can be used to control the distance between the ligand and the polymer molecule. Suitable spacer molecules include dialdehydes and dicarboxylic acids and their derivatives, whose functional groups are connected with one to four carbon atoms by alkylene bridges. A preferred spacer according to the present invention is glutardialdehyde.

The adducts of the macromolecular agent and the ligand react spontaneously with isolated, stroma-free, preferably deoxygenated hemoglobin, thus forming macromolecular agent-ligand-hemoglobin conjugates which are stable and have a high binding constant, and which are held together by non-covalent bonds between the ligand and the phosphate bond site of the hemoglobin.

Figure 1:
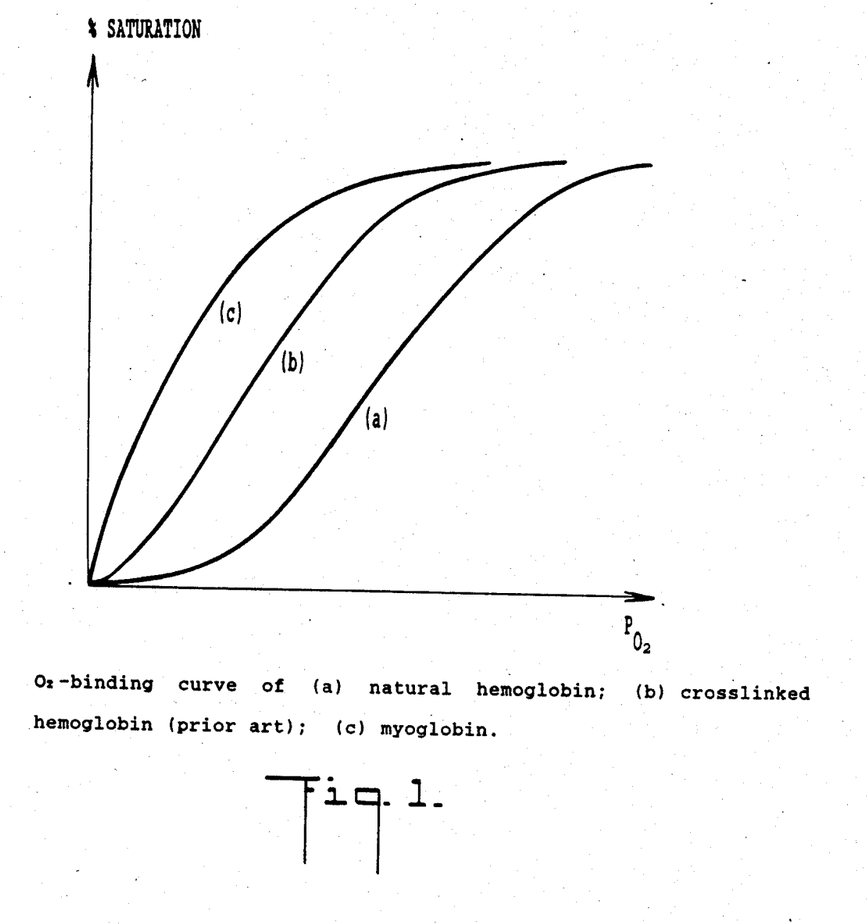
FIG. 1 shows the oxygen binding curves of natural hemoglobin, crosslinked hemoglobin and myoglobin which are functions of the percent saturation relative to the partial pressure of oxygen.

These conjugator complexes are able to bind and release oxygen reversibly. The oxygen affinity of hemoglobin modulated with the adduct is reduced, as demonstrated by the central portion of the oxygen dissociation curves, which shift to the right, that is, to a higher partial pressure of oxygen (FIGS. 2–5). The compositions of the invention retain the cooperativity of the hemoglobin subunits in oxygen uptake and release, as is reflected in the sigmoidal shape of the corresponding oxygen dissociation curve (FIGS. 2–5). FIG. 1 demonstrates the oxygen binding curve of natural hemoglobin, the crosslinked hemoglobin of the prior art, and myoglobin.

The hemoglobin conjugates of the invention can be used as hemoglobin-containing blood substitutes or plasma extenders with an oxygen-transferring function; due to their increased molecular weight, they have a long intravasal half-life. They are able to reversibly bind and release molecular oxygen, due to a relatively low oxygen affinity. Furthermore, the hemoglobin tetramer structure is not substantially disturbed by cross-linkage or complex formation in achieving these effects.

The properties of such hemoglobin conjugates can be varied within several parameters. The half-life in circulation can be controlled by varying the chemical nature and the properties of the conjugator used, such as molecular weight, solubility, or degree of cross-linkage. In addition, the strength of the bond between the polymer-ligand adduct and hemoglobin can be influenced by the number of negatively charged groups (e.g. phosphate groups) on the ligand.

The concentration of the ligand, i.e. the degree to which the macromolecular agent is loaded with the ligand, affects the maximum quantity of hemoglobin that can be bound non-covalently. The ligand concentration can therefore exert a direct influence on the oxygen transport capacity of the hemoglobin.

Compositions having different properties can be obtained by varying the distance between the ligand and macromolecular agent or the nature of the bond by which the two are linked. Here, either direct linkage or linkage through a spacer is possible; also, the nature of the bond (ether bond, phosphatic acid diester bond, etc.) influences the properties of the conjugates.

Lastly, several ligands (with or wihout spacer) and hence also several hemoglobin molecules may be bound to each macromolecular agent. Possible alternatives include one ligand-hemoglobin conjugate at each of the two ends of a polymer molecule and several ligand-hemoglobin conjugates at the side chains of a branched polymer.

Another alternative employs a two- or multi-phase macromolecular agent-ligand-hemoglobin system in which a solid, insoluble macromolecular agent contains several ligand molecules bound at the surface, possibly with interposition of a spacer, which allows the binding of several hemoglobin molecules. Examples of this are liposomes or emulsions to which the ligand-hemoglobin conjugates are bound in the nonaqueous phase. The ligands as well as hemoglobin are present in the aqueous phase, the ligands being linked through the non-aqueous phase.

Under the present invention it is possible to modify hemoglobin additionally with the usual bi- or poly-functional cross-linking agents. This procedure, however, alters the properties of the hemoglobin solutions in the disadvantageous manner known in the art, i.e. the oxygen affinity is clearly increased in comparison with the uncross-linked preparation, and there is a reduction in the cooperativity of the hemoglobin subunits with respect to their bonding affinity for molecular oxygen. But the conjugate formation between the macromolecular agent, the modulating ligand, and hemoglobin leads to a definite reduction of the oxygen affinity and a restoration of the cooperativity of the sub-units so that the compositions according to the invention which contain cross-linked hemoglobin are clearly superior to the cross-linked hemoglobin blood substitutes known in the art.

To prepare conjugates of an adduct and hemoglobin according to the invention, first, the macromolecular agents are synthesized or obtained commercially and chemically modified by known methods. Thus, for example, unmodified polyethylene glycols, their glycidyl ethers, or their alpha, omega-diamino-substituted derivatives may be used.

The macromolecular agent component of the invention is reacted with a ligand under controlled conditions of pH, temperature, and concentration in solutions with or without buffers. Preferred buffers are sodium-borate buffer (pH 9.0) or phosphate buffer (pH 7.2), but other buffer systems known in the art can also be used.

The end products are physiologically acceptable, water-soluble adducts, comprising macromolecular agents with molecular weights in the range of from 400 D to 500,000 D, to which phosphate-containing ligands are bound in the terminal position.

The resulting anionic adducts of the macromolecular agent to anionic ligands can be purified by methods known in the art, such as by diafiltration against water, where a molecular weight of from about 400 D to about 500,000 D can be selected by virtue of the exclusion limit of the filtering membrane.

The isolation on a relatively large scale of functionally intact hemoglobin (HbA) from human whole blood is known. Methods in Enzymology, volume 76, pp. 97 ff. The hemoglobin is strippd of endogenous ligands, suspended in an aqueous buffer solution, preferably in phosphate buffer (pH 7.4), and deoxygenated by repeated evacuation of the solution and subsequent washing with purified nitrogen.

The resulting hemoglobin-containing solution is mixed with aqueous, possibly buffered, solutions of the macromolecular agent-ligand adduct at pH values between 5.0 and 8.0. An acid pH range is preferred. This leads to the spontaneous formation of stable conjugates between the macromolecular agent-ligand compounds and hemoglobin, bound non-covalently.

The buffered solutions of the conjugate compositions of the invention have a clearly improved oxygen affinity as compared to cross-linked hemoglobins. The hemoglobin bound to macromolecular adducts is comparable with or even superior to the natural, erythrocyte-bound hemoglobin in terms of oxygen partial pressure at 50% saturation ($P_{50}$).

As can be seen from FIGS. 2 to 5, the conjugates of the invention also exhibit a high cooperativity of the hemoglobin subunits with respect to the binding and release of molecular oxygen. In the figures this cooperativity is evident from the sigmoidal form of the oxygen binding curve, for which the Hill coefficient approximates the natural value.

Furthermore, the intravasal half-life of the hemoglobin is greater for the conjugated form than for stromafree hemoglobin. The half-life for free, unmodified hemoglobin is approximately 85 to 100 minutes (Baldwin et al., Med. Lab. Sci. 39:45 (1982)), while for the conjugate compositions of the invention, half lives of up to several days have been measured.

The conjugate compositions of the invention have other beneficial properties including colloid osmotic pressure, rheological properties, stability, and storage.

The conjugate compositions of the invention can be administered to a patient with physiologically acceptable carriers, including adjuvants or additives such as Ringer lactate solution which are known in the art.

The following examples illustrate certain aspects of the invention but they do not limit the invention as set forth in the specification and claims.

EXAMPLE 1

Synthesis of an Adduct of Adenosin-5-Triphosphate (ATP) and BHP Dextran 70

1 g lyophilized BHP dextran (3-bromo-2-hydroxypropyl dextran) was dissolved at room temperature in 5 ml sodium borate buffer 0.1 M, pH 9.0, and the pH value was adjusted to pH 11.0 with 0.5 M NaOH. After 15 minutes, 500 micromoles adenosin triphosphate (ATP) dissolved in 5 ml of the same buffer was added to the BHP dextran solution. The pH value was corrected to pH 10.0 with solid NaHCO3, and incubation at room temperature was continued for another 24 hours with agitation. Unreacted activated groups were stirred with 0.1 M aqueous glycerin solution for 10 hours, in order to block them, and the reaction mixture was purified by diafiltration against water through an Amicon H 1 P 10 hollow fiber membrane (exclusion limit: 10,000). The retentate was lyophilized. The white product (0.8 g) had an ATP content of 0.18 m mole/g.

EXAMPLE 2

Synthesis of an Adduct of Inosital Hexaphosphate Sodium Salt (IHP) and BHP Dextran 70

Instead of the ATP employed in Example 1, 5 mM inositol hexaphosphate (IHP) sodium salt was reacted with 1 g BHP dextran and worked up. A white product (0.6 g) having an IHP content of 0.095 mol/g was obtained.

EXAMPLE 3

Preparation of Polymer-Ligand - Hemoglobin Conjugates (a) The products prepared according to Examples 1 and 2 were dissolved at a concentration corresponding to 1 mM equivalent ATP or 10 mM equivalent IHP, respectively, in 100 ml 0.1 M phosphate buffer, pH 7.3, and mixed with deoxygenated human hemoglobin (HbA) prepared according to Methods in Enzymology, vol. 76, pp. 97 ff so that a final concentration of the HbA of 6% was obtained.

Figure 2:
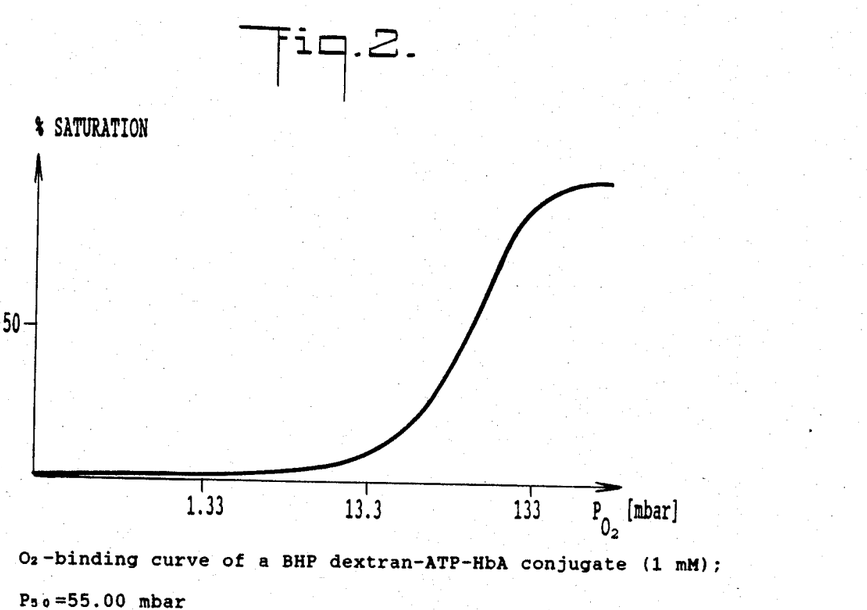
FIG. 2 shows the oxygen binding curve of a BHP dextran-ATP-HbA conjugate (concentration of 1 mM) as a function of the percent saturation relative to the partial pressure of oxygen.
Figure 3:
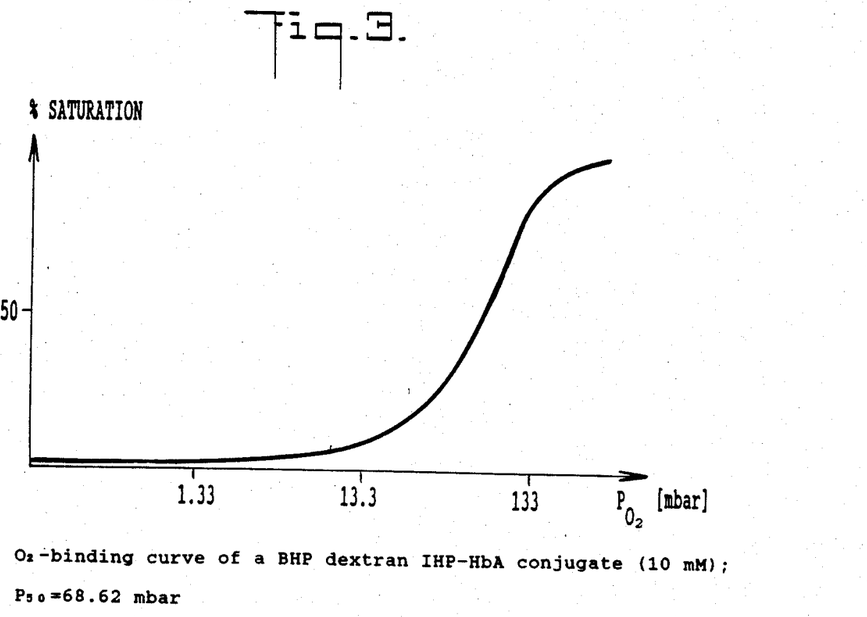
FIG. 3 shows the oxygen binding curve of BHP dextran-IHP-HbA conjugate (concentration of 10 mM) as a function of the percent saturation relative to the partial pressure of oxygen.

The oxygen binding curves of these mixtures, measured at pH 7.4 and 37° C. in BISTRIS buffer, are shown in FIG. 2 and FIG. 3. The $P_{50}$ values of the ATP and IHP preparations were 55.00 mbar and 68.32 mbar, respectively.

(b) In an experiment analogous to Example 3(a), the concentration of the BHP dextran-ATP adduct was adjusted to 0.2 mM equivalent ATP, and the concentration of the dextran-bound ligand BHP dextran-IHP was adjusted to 1.0 mM equivalent IHP.

Figure 4:
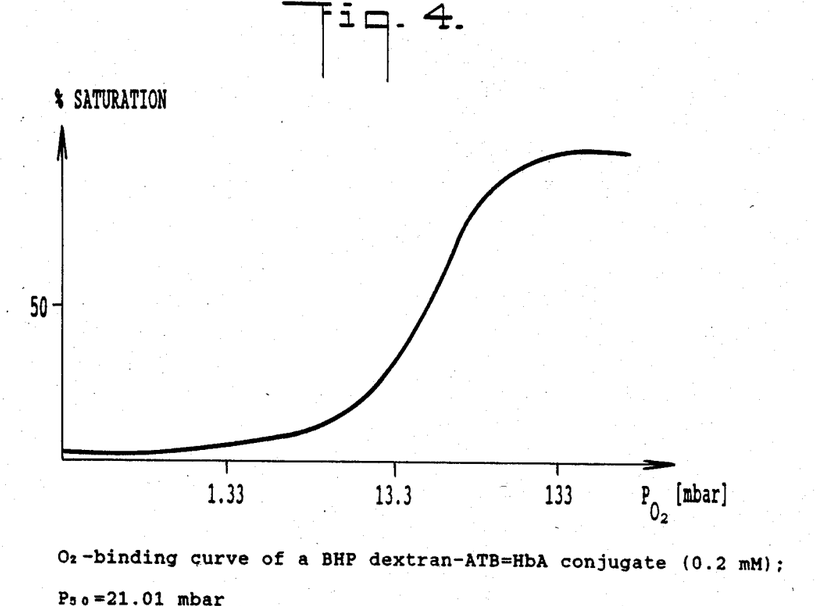
FIG. 4 shows the oxygen binding curve of a BHP dextran - ATB-HbA conjugate (concentration of 0.2 mM) as a function of the percent saturation relative to the partial pressure of oxygen.
Figure 5:
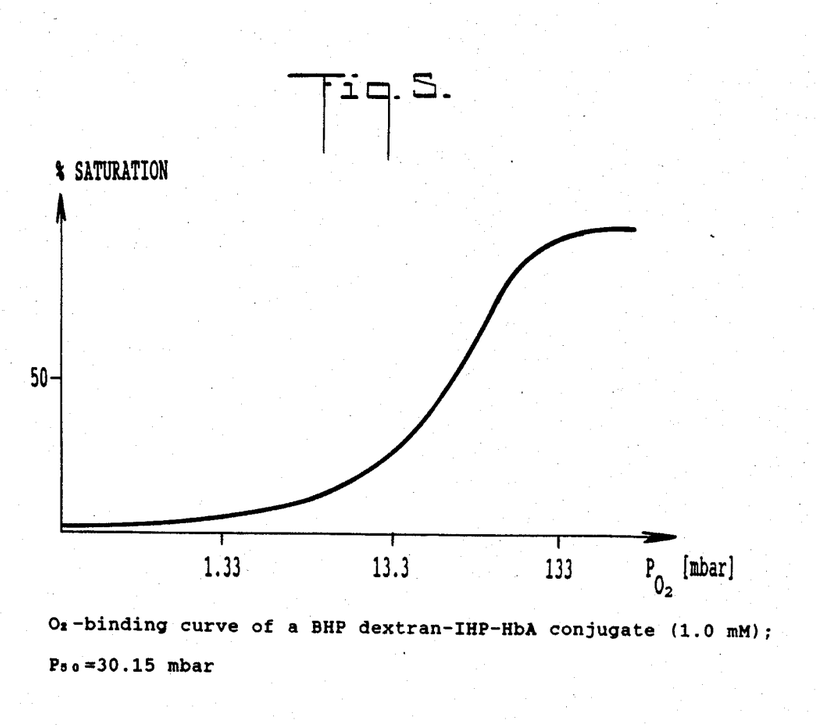
FIG. 5 shows the oxygen binding curve of BHP dextran-IHP-HbA) conjugate (concentration of 1.0 mM) as a function of the percent saturation relative to the partial pressure of oxygen.

FIGS. 4 and 5 show the respective oxygen binding curves, measured at pH 7.4 and 37° C. in BISTRIS buffer. The $P_{50}$ values of these hemoglobin-adduct conjugate preparations were 21.01 mbar and 30.15 mbar respectively.

(c) 200 ml of an 18% HbA solution, dissolved in 0.1 ml phosphate buffer, pH 7.4, was deoxygenated by repeatedly evacuating and washing with nitrogen. To this was added 1.0 g of the BHP dextran-IHP conjugate prepared according to Example 2, and the pH value was adjusted to 6.8. Under inert gas, 7.2 ml of a 5% glutardialdehyde solution was added and stirred for 30 minutes and the product was reduced by adding of 0.4 g NaBH4. The reaction mixture was diafiltered through an ultrafiltration membrane with an exclusion limit of 10,000 (HlP10 Hollowfiber) with continuous addition of 0.1 M phosphate buffer, pH 7.4, for 6 hours, and the mixture was adjusted to a hemoglobin concentration of 6%. The half-saturation pressure of this preparation was $P_{50}$=47.9 mbar.

(d) As described by Cohan and Haas, J.A.C.S. 75:1733 (1953), 1 mmole polyethylene glycol 10,000 was reacted with 20 mg tin-IV chloride in 200 ml xylene with 2 mmole epichlorhydrin, and was processed, omitting the fractional distillation step. The product was 9.2 g of the diglycidyl ether of the polyethylene glycol.

Under the conditions described in Example 1, 1 g (0.2 mmole) of the material was reacted in borate buffer with 0.5 mmole ATP for 10 hours at room temperature. The product was purified by diafiltration for 6 hours with water through a hollow fiber ultrafiltration membrane (H 1 P 5) and lyophilized. As described in Example 3(a), 10 mmole equivalent ATP of the ATP-PEG adduct was mixed with deoxygenated HbA at the final concentration of 6%, and the O2 binding curve was recorded. The $P_{50}$ value was 48.15 mbar.

(e) Following the specification given by Kern et al. in Makromol. Chem. 180:2539-2542 (1979), first the alpha, omega-diamino-substituted polyethylene glycol was prepared from polyethylene glycol 400 via the alpha, omega-ditosylate and reaction with ethanolamine.

40 g (10 mmole) of the alpha, omegadiaminopolyethylene glycol were dissolved in 1000 ml 0.1 M phosphate buffer, pH 7.2, and 8.0 g (30 mmole) pyridoxalphosphate were added while stirring. The substance was allowed to react overnight at room temperature; it was then reduced with 1.9 g NaBH4 at room temperature for 2 hours. The product was purified by diafiltration with water through a hollow fiber membrane H 1 P 1 (exclusion limit: 1,000), until pyridoxal phosphate could no longer be demonstrated in the ultrafiltrate by spectral photometry. The product was lyophilized (yield 73%), and reacted with deoxygenated HbA according to Example 3. This resulted in a product with an Hb concentration of 6% and a PEG-(pyridoxalphosphate)2 concentration of 2.5 mM (10 g/liter), with a P50 value of 54.33 mbar.

While there have been described what are presently believed to be preferred embodiments of the invention, it will be apparent to one skilled in the art that numerous changes can be made in the ingredients, conditions and proportions set forth in the foregoing embodiments without departing from the invention as described herein and as defined in the amended claims.

What is claimed is:

1. An allosterically active conjugate composition of hemoglobin which comprises at least one tetramer of hemoglobin and at least one adduct of a physiologically acceptable polymeric agent non-toxic to biological systems covalently linked to at least one ligand such that the adduct is bound to the allosteric binding site of the hemoglobin in a reversible, non-covalent manner and the ligand does not contain any reactive functional group that would be capable of reacting covalently with the hemoglobin.

2. The composition according to claim 1, wherein the polymeric agent is a water-soluble polymer, the hemoglobin is hemoglobin A substantially free of endogenous ligands, and the ligand is anionic.

3. The composition according to claim 1, wherein the molecular weight of the polymeric agent is from about 400 D to about 500,000 D.

4. The composition according to claim 1, wherein the polymeric agent is a water soluble polymer with a molecular weight from about 400 D to about 50,000 D.

5. The composition according to claim 1, wherein the physiologically acceptable polymeric agent is selected from the group consisting of polyvinylpyrolidone, dextran, a polyvinyl alcohol, a soluble starch, a hydroxyalkyl starch, a polypropylene glycol, a mucopolysaccharide, polyethylene glycol or a copolymer thereof, a liposome, a protein, surfactant, a polymethylacrylate, an emulsion of oil in water, and derivatives of said compounds.

6. The composition according to claim 1, wherein the ligand is selected from the group consisting of an inositol phosphate, an inositol sulfate, a nucleotide phosphate, a pyridoxal phosphate, a pyridoxal sulfate, a sulfated mucopolysaccharide, a beta-naphthol phosphate, salicylic acid, p-hydroxybenzoic acid, an aromatic aldehyde, a benzenesulfonic acid, and derivatives of said compounds.

7. The composition according to claim 1, wherein the polymeric agent is selected from the group consisting of 3-bromo-2-hydroxypropyl dextran, alpha, omega-disubstituted derivatives of polyethlene glycol, and diglycidyl ether of polyethylene glycol.

8. The composition according to claim 1, wherein the ligand is selected from the group consisting of sodium inositol hexaphosphate, adenosin triphosphate, fructose-1, 6-diphosphate, and 4-isothio-cyanate-benzenesulfonic acid.

9. The composition according to claim 1, wherein the ligand and polymeric agent molecule are separated by a spacer molecule to which both are covalently bonded.

10. The composition according to claim 9, wherein the spacer molecule is selected from the group consisting of dialdehydes and dicarboxylic acids and their derivatives, whose functional groups are connected with one to four carbon atoms by alkylene bridges.

11. The composition according to claim 1, wherein the hemoglobin is cross-linked intramolecularly or intermolecularly by means of at least one cross-linking agents.

12. The composition according to claim 1, further comprising a physiologically acceptable carrier in combination with the hemoglobin and adduct.

13. A method for the production of conjugate compositions of hemoglobin and adduct which comprises the steps of:
    (a) covalently linking by known methods a ligand to a polymeric agent non-toxic to biological systems thereby forming an adduct such that the ligand does not contain any reactive functional group reactive with hemoglobin;
    (b) purifying the adduct; and
    (c) mixing the adduct with purified human hemoglobin A isolated and separated from endogenous ligands in aqueous solution at room temperature and permitting the adduct and hemoglobin A to form a non-covalent bond between them.

14. The method according to claim 13, wherein the polymeric agent is selected from the group consisting of polyvinyl pyrrolidone, dextran, polyvinyl alcohol, soluble starch, hydroxyalkyl starch, mucopolysaccharide, polyethylene glycol or a copolymer thereof, protein, surfactant, polymethacrylate, polymethyl acrylate, a liposome, an emulsion of oil in water and derivatives of said compounds.

15. The method according to claim 13, wherein the ligand is selected from the group consisting of sugar phophate, inositol phosphate, inositol sulfate, nucleotide phosphate, pyridoxal phosphate, pyridoxal sulfate, a salicylicacid, a phydroxybenzoic acid, aromatic aldehyde, benzenesulfonic acid, and derivatives of said compounds.

16. The method according to claim 13, wherein the hemoglobin is deoxygenated.

17. The method according to claim 13, wherein the step of purifying the adduct is achieved by means of diafiltering the adduct.

18. The method according to claim 13, wherein the aqueous solutions are buffered.

19. The method according to claim 13, wherein the pH value ranges from about 5.0 to about 8.0.

20. The method according to claim 13, wherein the pH value is acidic.

21. The method according to claim 13, wherein the hemoglobin is cross-linked intramolecularly or intermolecularly by means of at least one cross-linking agents.

22. The method according to claim 13, wherein the macromolecular agent has a molecular weight from about 400 D to 500,000 D.

23. The method according to claim 13, wherein a spacer molecule is additionally used in the reaction of covalently linking macromolecular agent and ligand.

24. The method according to claim 13, wherein the hemoglobin is hemoglobin A, the polymeric agent is selected from the group consisting of 3-bromo-2-hydroxypropyl dextran, alpha, omega-disubstituted derivatives of polyethylene glycol and diglycidyl ether of polyethylene glycol and the ligand is selected from the group consisting of sodium inositol hexaphosphate, adenosin triphospshate, fructose-1, 6-diphosphate and 4-isothio-cyanatebenzenesulfonic acid.

25. The composition according to claim 1, wherein the polymeric agent is selected from the group consisting of a polysaccharide and a polyol.

26. The composition according to claim 13, wherein the polymeric agent is selected from the group consisting of a polysaccharide and a polyol.

* * * * *

UNITED STATES PATENT AND TRADEMARK OFFICE
CERTIFICATE OF CORRECTION

PATENT NO. :     4,698,387

DATED      :     October 6, 1987

INVENTOR(S) :    Karl-Heinz Schmidt, et al.

It is certified that error appears in the above-identified patent and that said Letters Patent is hereby corrected as shown below:

Column 1, line 52, delete "Offenlegenschrift" and substitute therefor --Offenlegungsschrift--.

Column 1, lines 65-66, delete "Offenleigen-schrift" and substitute therefor --Offenlegungsschrift--.

Column 2, line 5, delete "Offenlegenschrift" and substitute therefor --Offenlegungsschrift--.

Column 2, line 8, delete "Offenlegenschrift" and substitute therefor --Offenlegungsschrift--.

Column 2, line 57, delete "Offenlegenschrift" and substitute therefor --Offenlegungsschrift--.

Column 2, line 62, delete "Offenlegenschrift" and substitute therefor --Offenlegungsschrift--.

Column 2, lines 60-61, delete "diphospeoglyceate" and substitute therefor --diphosphoglyceate--.

Column 4, line 12, delete "polyvinylprolidone" and substitute therefor --polyvinylpyrrolidone--.

Column 4, line 51, delete "tolphosphates" and substitute therefor --tholphosphates--.

Column 4, line 51, delete "p-hydroxygenzoic" and substitute therefor --p-hydroxybenzoic--.

UNITED STATES PATENT AND TRADEMARK OFFICE
CERTIFICATE OF CORRECTION

PATENT NO. :   4,698,387

DATED      :   October 6, 1987

INVENTOR(S) :  Karl-Heinz Schmidt, et al.

It is certified that error appears in the above-identified patent and that said Letters Patent is hereby corrected as shown below:

Column 4, line 57, delete "hexaphosphahte" and substitute therefor --hexaphosphate--.

Column 6, line 50, delete "strippd" and substitute therefor --stripped--.

Column 8, line 21, delete "of".

Column 9, line 30, delete "polyvinylpyrolidone" and substitute therefor --polyvinylpyrrolidone--.

Column 9, line 68, delete "agents" and substitute therefor --agent--.

Column 10, line 20, delete "polyvinyl pyrrolidone" and substitute therefor --polyvinylpyrrolidone--.

Column 10, line 46, delete "agents" and substitute therefor --agent--.

Column 10, line 60, delete "triphospsate" and substitute therefor --triphosphate--.

Signed and Sealed this

Twenty-first Day of March, 1989

Attest:

DONALD J. QUIGG

*Attesting Officer*　　　*Commissioner of Patents and Trademarks*